United States Patent
Engelbart et al.

(10) Patent No.: US 7,617,714 B2
(45) Date of Patent: *Nov. 17, 2009

(54) PSEUDO POROSITY REFERENCE STANDARD FOR CORED COMPOSITE LAMINATES

(75) Inventors: Roger W. Engelbart, St. Louis, MO (US); Christopher M. Vaccaro, O'Fallon, MO (US); April L. Beisiegel, Freeburg, IL (US)

(73) Assignee: The Boeing Company, Chicago, IL (US)

( * ) Notice: Subject to any disclaimer, the term of this patent is extended or adjusted under 35 U.S.C. 154(b) by 152 days.

This patent is subject to a terminal disclaimer.

(21) Appl. No.: 11/567,673

(22) Filed: Dec. 6, 2006

(65) Prior Publication Data

US 2008/0134749 A1 Jun. 12, 2008

(51) Int. Cl.
*G01N 29/30* (2006.01)
(52) U.S. Cl. .................. 73/1.86; 73/1.03; 73/1.82
(58) Field of Classification Search ............ 73/1.86, 73/1.82, 1.03; 436/8
See application file for complete search history.

(56) References Cited

U.S. PATENT DOCUMENTS

| | | | |
|---|---|---|---|
| 3,784,043 A * | 1/1974 | Presnick | 220/4.28 |
| 3,908,439 A | 9/1975 | Peiak, et al. | |
| 3,933,026 A | 1/1976 | Ham | |
| 4,156,123 A | 5/1979 | Fischer et al. | |
| 4,173,139 A * | 11/1979 | Conn | 73/1.84 |
| 4,266,154 A | 5/1981 | Marshall | |
| 4,286,455 A | 9/1981 | Ophir et al. | |
| 4,393,987 A * | 7/1983 | Anderson et al. | 228/157 |
| 4,406,153 A | 9/1983 | Ophir et al. | |
| 4,445,360 A | 5/1984 | Treder, Jr. | |
| 4,466,270 A * | 8/1984 | Kimura et al. | 73/1.86 |
| 4,566,330 A | 1/1986 | Fujii et al. | |
| 4,660,419 A | 4/1987 | Derkacs | |
| 4,674,334 A | 6/1987 | Chimenti et al. | |
| 4,729,235 A | 3/1988 | Podlech | |
| 4,747,295 A | 5/1988 | Feist et al. | |

(Continued)

FOREIGN PATENT DOCUMENTS

DE 28 14 336 5/1979

(Continued)

OTHER PUBLICATIONS

The Boeing Company, PCT/US2007/086465, ref. 06-0810, mailed Jun. 30, 2008.

*Primary Examiner*—J M Saint Surin
(74) *Attorney, Agent, or Firm*—Rozenblat IP LLC (57) ABSTRACT

The invention relates to pseudo porosity standards, and methods for their manufacture and use, which substantially mimic the effect porosity has on ultrasonic sound as it passes through a cored composite laminate having porosity. An ultrasonic inspection reference standard for cored composite laminates having porosity may include a member having at least one thickness, at least one core, and at least one mesh. The member may be manufactured from a fiber-free polymer resin using a stereo lithography process. Use of the mesh may produce a standard which transmits ultrasonic energy, with the mesh scattering and attenuating the energy. Use of the core may aide in modeling a cored composite laminate. The manufactured reference standard may replace more costly porous, cored, composite laminate reference standards in the aircraft industry and in other non-aircraft applications.

32 Claims, 7 Drawing Sheets

U.S. PATENT DOCUMENTS

| | | | |
|---|---|---|---|
| 4,779,452 | A | 10/1988 | Cohen-Tenoudji |
| 5,054,310 | A | 10/1991 | Flynn |
| 5,065,520 | A | 11/1991 | Kaminagun |
| RE33,789 | E | 1/1992 | Stevenson |
| 5,127,268 | A | 7/1992 | Kline |
| 5,163,027 | A | 11/1992 | Miller et al. |
| 5,163,077 | A | 11/1992 | Dupre et al. |
| 5,196,343 | A * | 3/1993 | Zerhouni et al. ............ 436/8 |
| 5,238,556 | A | 8/1993 | Shirkhan |
| 5,312,755 | A | 5/1994 | Madsen et al. |
| 5,525,385 | A | 6/1996 | Weinstein et al. |
| 5,637,175 | A | 6/1997 | Feygin et al. |
| 5,656,763 | A | 8/1997 | Flax |
| 5,662,566 | A | 9/1997 | Marxrieser et al. |
| 5,837,880 | A | 11/1998 | Shakinovsky et al. |
| 6,238,343 | B1 | 5/2001 | Madsen et al. |
| 6,405,583 | B1 | 6/2002 | Shirakawabe et al. |
| 6,415,051 | B1 | 7/2002 | Callari et al. |
| 6,415,644 | B1 | 7/2002 | Rockwood et al. |
| 6,426,274 | B1 | 7/2002 | Tayanaka |
| 6,649,516 | B2 | 11/2003 | Asakawa et al. |
| 6,684,701 | B2 | 2/2004 | Dubois et al. |
| 6,803,095 | B1 | 10/2004 | Halladay et al. |
| 6,843,945 | B1 | 1/2005 | Hsai-Yin Lee |
| 6,925,145 | B2 | 8/2005 | Batzinger |
| 6,959,602 | B2 | 11/2005 | Peterson, Jr. et al. |
| 6,962,701 | B2 | 11/2005 | Koenig |
| 6,962,739 | B1 | 11/2005 | Kim et al. |
| 7,010,980 | B2 | 3/2006 | Meier |
| 7,076,992 | B2 * | 7/2006 | Greelish ............ 73/1.86 |
| 7,188,559 | B1 | 3/2007 | Vecchio |
| 7,216,544 | B2 | 5/2007 | Vaccaro et al. |
| 7,320,241 | B2 | 1/2008 | Kollgaard et al. |
| 7,353,709 | B2 | 4/2008 | Kruger et al. |
| 7,357,014 | B2 * | 4/2008 | Vaccaro et al. ............ 73/1.86 |
| 7,418,860 | B2 | 9/2008 | Austerlitz, et al. |
| 7,424,818 | B2 | 9/2008 | Vaccaro, et al. |
| 7,509,832 | B2 | 3/2009 | Vaccaro et al. |
| 7,510,817 | B2 | 3/2009 | Benoit et al. |
| 2006/0090563 | A1 * | 5/2006 | Austerlitz et al. ......... 73/290 V |
| 2006/0213250 | A1 | 9/2006 | Vaccaro et al. |
| 2006/0234391 | A1 | 10/2006 | Weiss et al. |
| 2006/0265679 | A1 | 11/2006 | Scheffer et al. |
| 2007/0089479 | A1 * | 4/2007 | Vaccaro et al. ............ 73/1.86 |
| 2007/0107520 | A1 * | 5/2007 | Vaccaro et al. ............ 73/649 |
| 2007/0119256 | A1 * | 5/2007 | Vaccaro et al. ............ 73/649 |
| 2007/0125177 | A1 * | 6/2007 | Vaccaro et al. ............ 73/649 |
| 2007/0128435 | A1 * | 6/2007 | Hiel et al. ............ 428/375 |
| 2008/0087093 | A1 * | 4/2008 | Engelbart et al. ............ 73/620 |
| 2008/0121039 | A1 * | 5/2008 | Vaccaro et al. ............ 73/600 |
| 2008/0134749 | A1 | 6/2008 | Engelbart et al. |
| 2008/0196475 | A1 | 8/2008 | Engelbart et al. |

FOREIGN PATENT DOCUMENTS

| | | |
|---|---|---|
| DE | 2814336 B1 | 5/1979 |
| GB | 2221991 A | 2/1990 |
| JP | 61265565 | 11/1986 |
| JP | 08210953 A | 8/1996 |
| WO | 90/13024 A1 | 11/1990 |

* cited by examiner

| | |
|---|---|
| Form | Electroformed Wire Cloth |
| Square/Rectangle Size | 0.00442" (112 Microns) |
| Mesh Per Inch Range | Fine Mesh |
| Mesh Per Inch (Fine) | 200 x 200 |
| Percentage of Open Area Range | 70 - 79 |
| Percentage of Open Area | 78 |
| Wire Diameter | 0.00058" |
| Thickness | 0.002" |

FIG. 9

| | |
|---|---|
| Material Type | Plastic |
| Plastic Type | Nylon |
| Form | Woven Thermoplastic Mesh |
| Square/Rectangle size | 0.0012" |
| Mesh Per Inch Range | Fine Mesh |
| Mesh Per Inch (Fine) | 361 x 361 |
| Percentage of Open Area Range | 10 - 19 |
| Percentage of Open Area | 18 |
| Thread Diameter | 0.0016" |

PSEUDO POROSITY REFERENCE STANDARD FOR CORED COMPOSITE LAMINATES

BACKGROUND OF THE INVENTION

Composite laminate reference standards are employed when performing ultrasonic inspection on cored composite laminate materials. They are used to aid in the detection of planar defects such as delaminations, foreign material, and the detection and quantification of porosity. A relationship exists between the strength of a composite laminate and the presence of defect conditions. This relationship is established in the course of effects-of-defects programs that look at the strength degradation of materials as a result of defects. Composite reference standards are currently manufactured with representative planar conditions to aid in the detection of delaminations and foreign material. It is difficult however to tie detection and quantification of porosity to a representative planar defect reference standard without the introduction of defects that mimic porosity.

Due to this difficulty, one approach to detecting and quantifying porosity in composite laminates has been to build a set of porosity reference standards for a given material. This set of standards, which are costly to build and certify for use, are used to qualify production inspection systems and are used to determine the operating characteristics of ultrasonic inspection systems. The introduction of new composite materials and the cost associated with qualifying new and existing ultrasonic inspection systems to inspect those materials has produced a need to build and qualify less expensive porosity standards. The standards, once produced, can be tied back to material properties via effects-of-defects programs and used to evaluate the strength characteristics of the materials being inspected.

SUMMARY OF THE INVENTION

In one aspect of the present invention, an ultrasonic inspection reference standard for cored composite laminates having porosity comprises a member having at least one thickness, at least one mesh, and at least one core. The member is manufactured from a fiber-free polymer resin.

In another aspect of the present invention, an ultrasonic inspection reference standard for cored composite laminates having porosity comprises a member having at least one thickness, at least one core, and at least one mesh. The reference standard is adapted to contain at least one of the acceptable and rejectable ultrasonic properties of a cored composite laminate having porosity.

In a further aspect of the present invention, an ultrasonic inspection process for cored composite laminates having porosity is provided. A reference standard is manufactured. The reference standard comprises a member having at least one thickness, at least one core, and at least one mesh. A cored composite laminate having porosity is inspected with an ultrasonic technique using the reference standard.

These and other features, aspects and advantages of the present invention will become better understood with reference to the following drawings, description and claims.

DETAILED DESCRIPTION OF THE INVENTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

Figure 1:
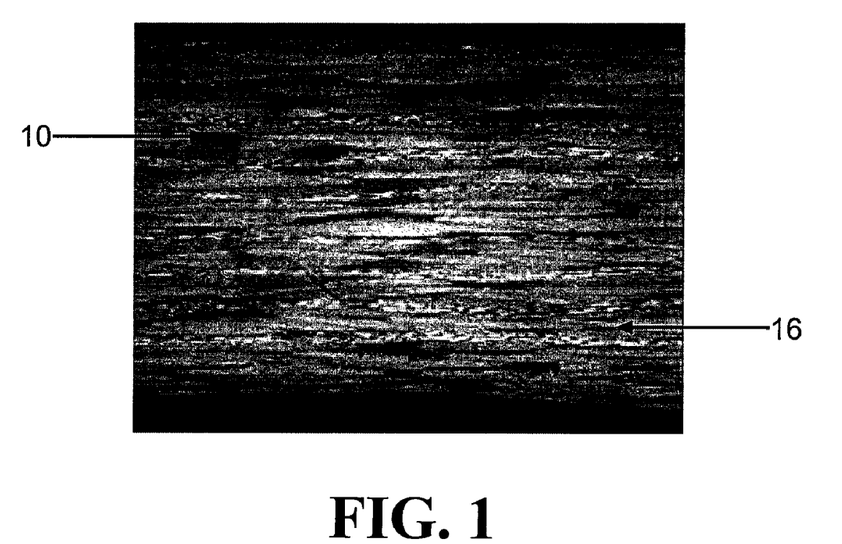
FIG. 1 is a photomicrograph of a composite laminate with porosity.
Figure 2:
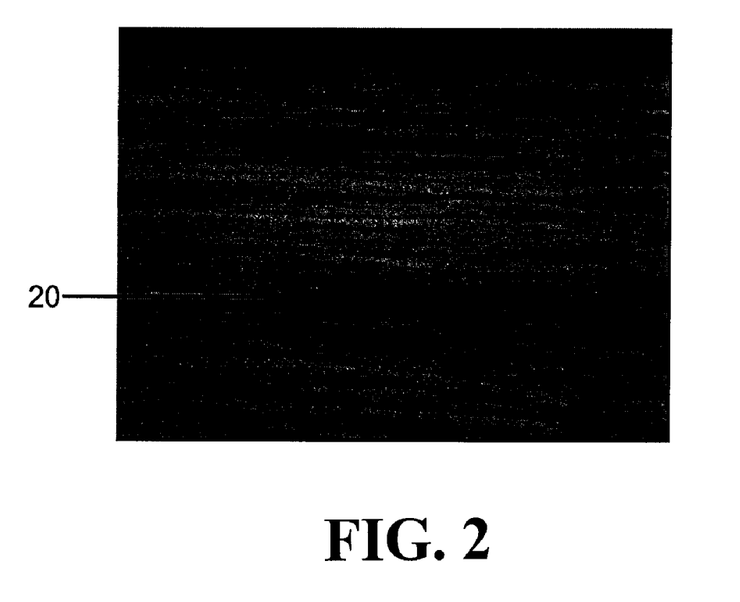
FIG. 2 is a photomicrograph of a composite laminate with large, planar-like porosity.

Composite laminates consist of two primary constituents including a fiber, and a resin matrix that bonds the fibers together. The fiber is typically graphite. Porosity in composite laminates is an unwanted product of the manufacturing cure cycle and is characterized by voids or a lack of resin within the laminate. FIG. 1 depicts a photomicrograph of a composite laminate with areas of porosity 10 shown as elliptical shapes that appear darker than the surrounding non-porous areas 16. The morphology and distribution of the porosity vary depending on a number of processing variables. The size of porosity also varies from relatively small diameters of 0.005" up to large planar conditions 20 like those illustrated in FIG. 2.

Figure 3:
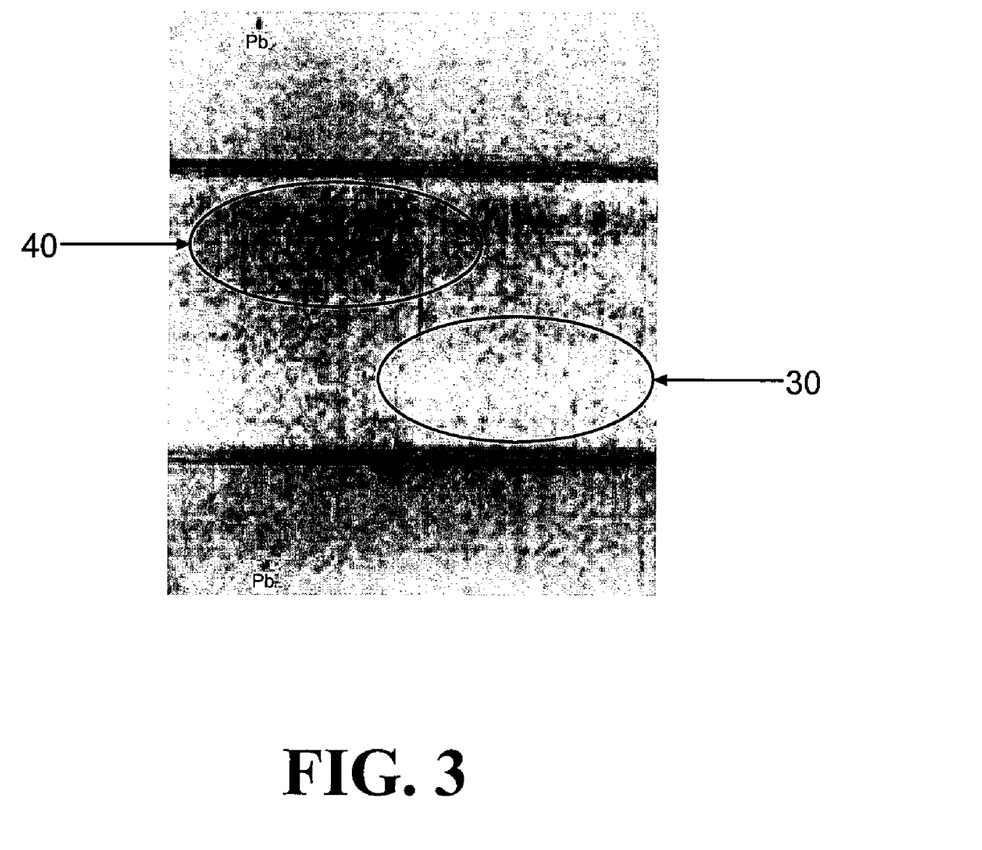
FIG. 3 is an ultrasonic C-scan of a composite laminate with porosity.

Porosity within a composite laminate may be quantitatively measured using high frequency ultrasonic methods. As the void content of a laminate increases, so does the ultrasonic attenuation. Ultrasonic attenuation is the combined loss of acoustic energy within the laminate which results from reflection and scattering of the sound pulse as it passes through the laminate. The ultrasonic C-scan in FIG. 3 illustrates this condition. The light gray areas 30 are where there is very little to no porosity in the laminate. The dark areas are where the laminate has porosity of some level.

Previous work has shown that photo-polymer resins used in stereo lithography (SLA), as well as conventional thermo set and thermoplastic resins like those used to bind fibers in composite laminates, have similar ultrasonic (acoustic) properties to graphite epoxy composite laminates. This is detailed in U.S. application Ser. No. 11/090,553, filed on Mar. 25, 2005, and titled Ultrasonic Inspection Reference Standard For Composite Materials, which is hereby incorporated by reference.

Figure 4:
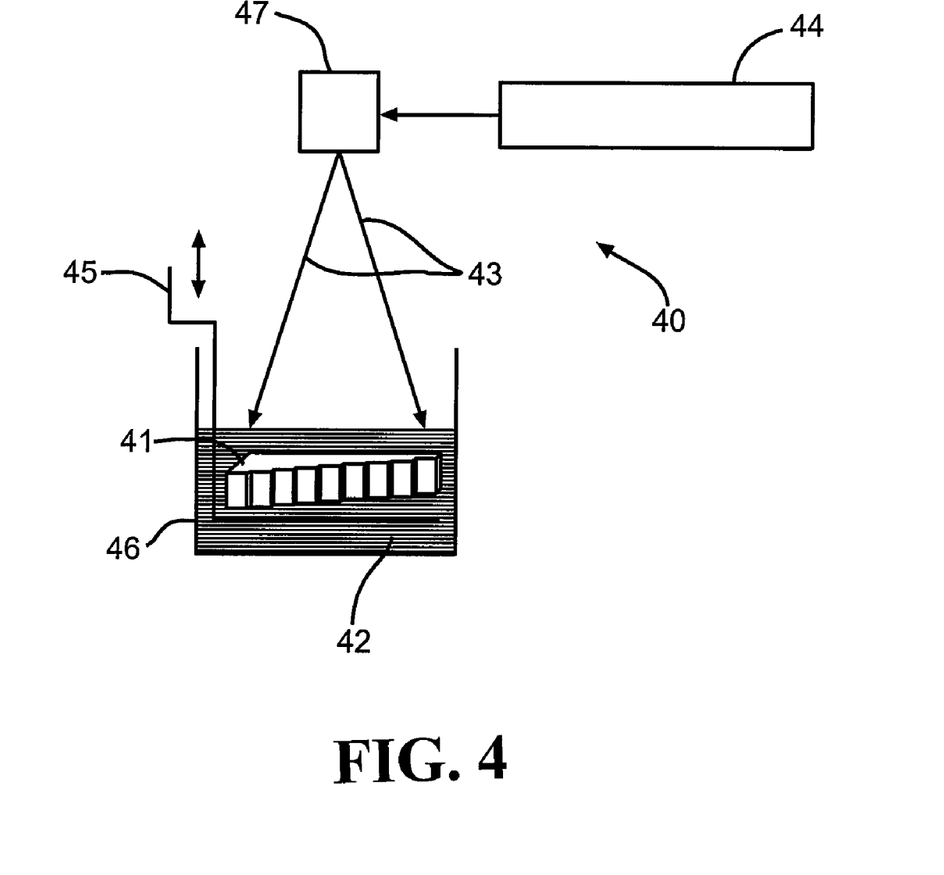
FIG. 4 is a front view of a stereo lithography process.

As shown in FIG. 4, the use of a stereo lithography process 40 may produce plastic parts 41, such as an ultrasonic inspection reference standard manufactured from a photo-polymer resin, directly from a 3D CAD (computer-aided design)

model. The surface of a liquid photopolymer 42 is solidified layer-by-layer using a laser beam 43 emitted by a laser 44. When the laser beam 43 hits the liquid photopolymer 42, it solidifies the resin. When a layer is fully traced, a movable table 45 is then lowered in the vat 46 of resin. A scanner system 47 directs the laser beam 43 according to a loaded CAD model. The self-adhesive property of the material causes the layers to stick with each other and in this way a three-dimensional part 41 is formed in multi-layers. The stereo lithography process 40 is accurate and suitable for smooth surface finished parts. Parts manufactured using the stereo lithography process 40 may be used, for example, for conceptual designs, product verification, pattern making. The stereo lithography process 40 may be used, for example, for rapid prototyping. Use of the stereo lithography process 40 may enable the manufacture of ultrasonic inspection reference standards, such as a polymer resin reference standard, with varying thicknesses and geometries that resemble the fiber-reinforced part to be inspected. The method of manufacturing an ultrasonic inspection reference standard from a fiber-free polymer resin may not require any tooling, and is not limited to the methods discussed.

To demonstrate the use of a fiber-free photo-polymer resin as a reference standard, a photo-polymer resin reference standard was manufactured with the same physical steps as a prior art graphite-epoxy reference standard by using the stereo lithography process 40 shown in FIG. 4. Both standards were then ultrasonically scanned at 5.0 MHz using both the through-transmission technique and the pulse-echo technique. The obtained data for the through-transmission technique is illustrated in the x-y plot 50 of FIG. 5, while the obtained data for the pulse-echo technique is illustrated in the x-y plot 60 of FIG. 6. The plots demonstrate attenuation 52 and 62 measured in decibels (dB) versus thickness 51 and 61 measured in inches. The attenuation is a decrease in intensity of a sound wave as a result of absorption and scattering of ultrasonic energy. The plots 50 and 60 include data points 53 and 63 for a photo-polymer resin reference standard free of fibers, and data points 54 and 64 obtained for a prior art graphite-epoxy reference standard.

Figure 5:
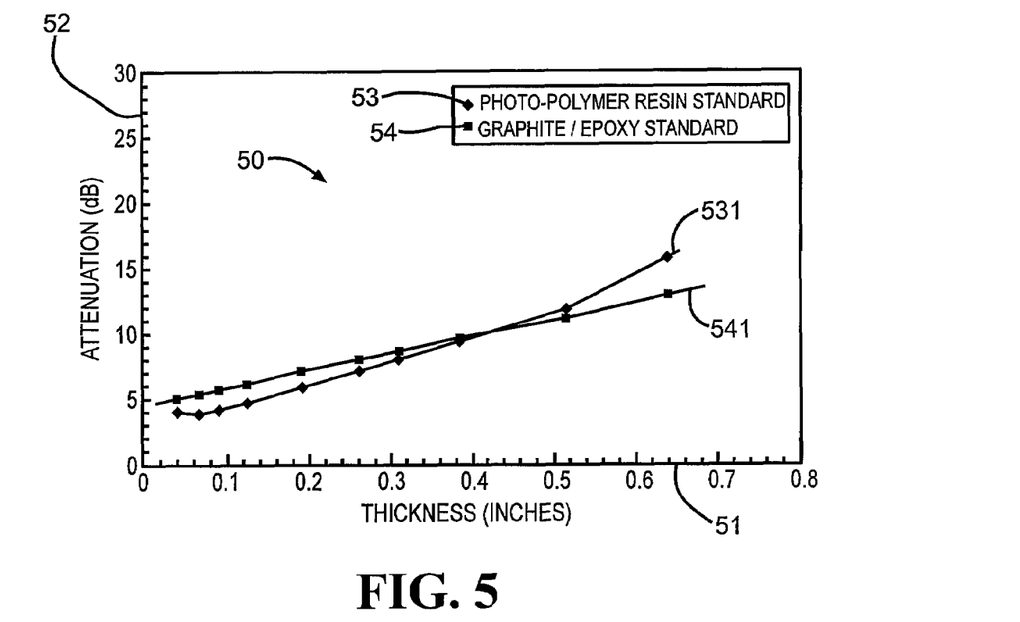
FIG. 5 is an x-y plot showing attenuation versus thickness applying through-transmission technique to both a photo-polymer resin standard and a graphite-epoxy standard.
Figure 6:
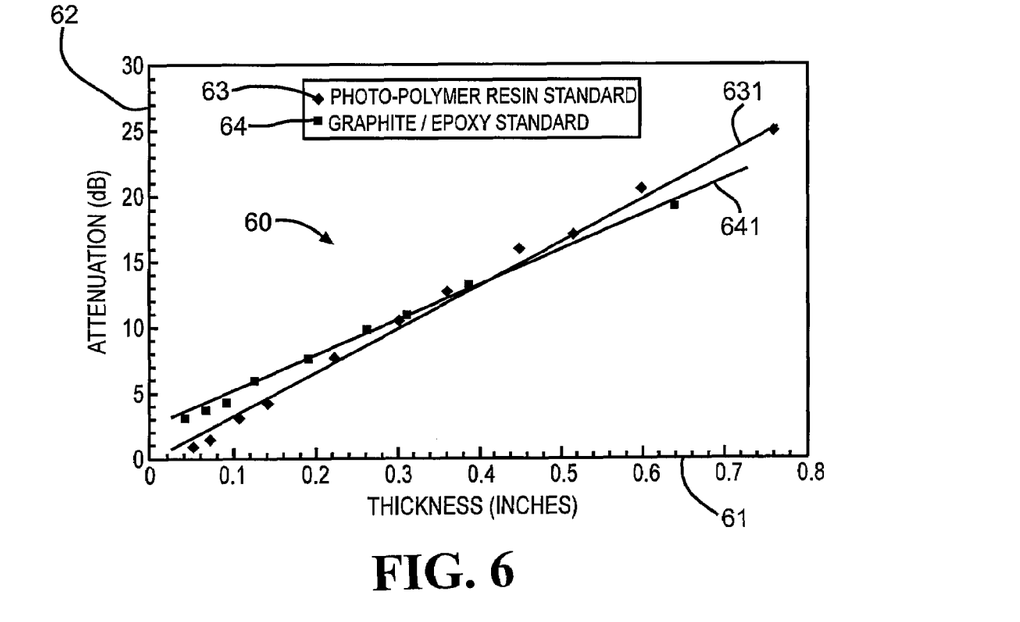
FIG. 6 is an x-y plot showing attenuation versus thickness applying pulse-echo technique to both a photo-polymer resin standard and a graphite-epoxy standard.

As shown in FIGS. 5 and 6, the slopes 531 and 631 of the photo-polymer resin standard is steeper than the slopes 541 and 641 of the prior art graphite-epoxy reference standard. However, the results are within the system noise, which is typically +/−2 dB. Consequently, the prior art graphite-epoxy reference standard may be substituted with the photo-polymer resin reference standard that is fiber-free. Since ultrasonic attenuation is material dependent, altering the thickness of the polymer resin reference standard may be used to bring the slopes 531, 541, 631, and 641 in line if needed. Using this approach, a fiber-free polymer resin reference standard may be designed to have an equivalent thickness based on the material properties of the fiber-reinforced composite part to be tested and not the actual thickness of a prior art fiber-reinforced composite reference standard.

The present invention relates to pseudo porosity standards, and methods for their manufacture and use, which substantially mimic the effect porosity has on ultrasonic sound as it passes through a cored composite laminate having porosity. For purposes of this application, a cored composite laminate is defined as a composite laminate having at least one core disposed in, within, or against the composite laminate. The term 'core' is defined as a member, which is made of a foam, honeycomb, or other core-type of material, which is disposed and/or sandwiched in a composite laminate. The term 'core' includes both singular and plural connotations. In a preferred embodiment of the invention, as discussed in more detail below, a pseudo porosity standard is manufactured using stereo lithography on a polymer resin to make a member having at least one thickness with similar acoustic properties of the cored composite laminate (fiber/resin combination). In order to model a cored composite laminate having porosity, at least one mesh and at least one core are incorporated into the member to produce a standard which transmits ultrasonic energy, with the mesh scattering and attenuating the energy, and the core modeling the core of the composite laminate. For instance, a porous composite laminate having a cored honeycomb material may be modeled by incorporating at least one mesh and at least one core, made of the honeycomb material, into the member. Preferably, a plurality of mesh and one core are disposed in alternating layers within the member. However, in other embodiments, any number and type of mesh and core may be disposed in any configuration in, on, or about the member. As an example, in one embodiment, multiple cores and mesh may be disposed in alternating layers within the member. For purposes of this application, a mesh is defined as an interwoven weave of one or more materials having at least partial openings dispersed in the weave, and the term includes both singular and plural connotations. The mesh may be made of one or more of wire, fiberglass, polymer, nylon, and a metallic material. In other embodiments, varying types of mesh may be used, and varying types of fiber-free polymer resin may be used, including the use of a polymer resin which is substantially similar to the resin of a composite material to be inspected. In still other embodiments, a non-stereo lithography process may be applied.

Figure 7:
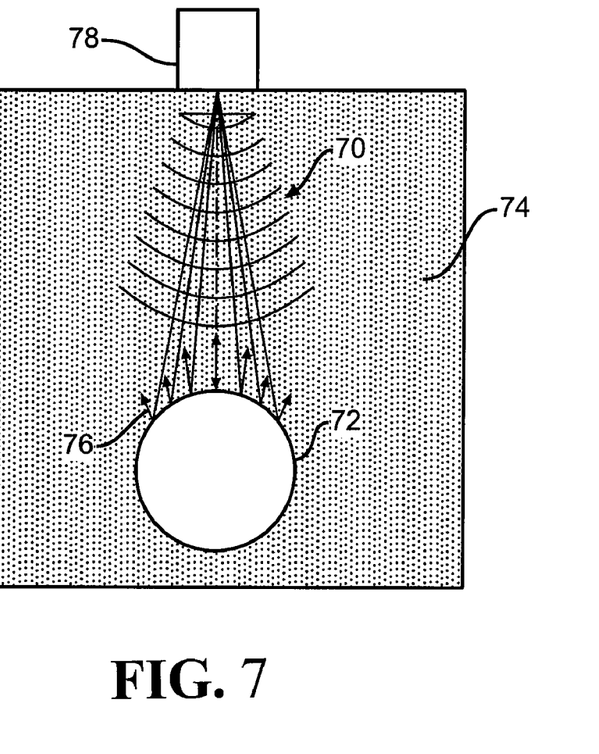
FIG. 7 is a simplified illustration of the ultrasonic two dimensional scattering which occurs off a circle.
Figure 8:
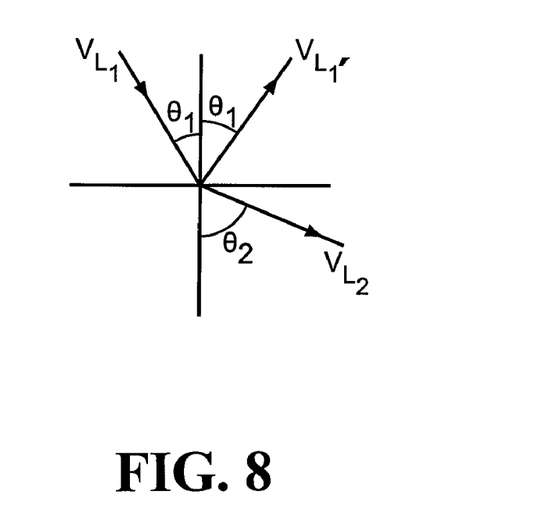
FIG. 8 depicts the principle of reflection and scattering under Snell's law.

The invention was arrived at in part due to the discovery that scattering of an ultrasonic pulse of energy can be produced through the placement of small voids within a homogenous median. This is the general principle for producing voids (porosity) within a composite laminate. Similarly, it was discovered that scattering can be accomplished through the introduction of hollow shafts in a homogenous median. The amount of ultrasonic scatter is dependent, in part, on the size of the shafts, the number of shafts and their proximity to one another. FIG. 7 is a simplified illustration of the ultrasonic two dimensional scattering 70 which occurs off a circle 72. In this example, the acoustic impedance mismatch between the base material 74, in this case a homogenous median, and the hollow circle 72, is large. This produces nearly 100 percent reflection 76 of the incident ultrasonic ray perpendicular to the ultrasonic transducer 78. As shown in FIG. 8, the principle of reflection and subsequent scattering is based on Snell's law as follows:

$$\frac{\sin\theta_1}{V_{L_1}} = \frac{\sin\theta_2}{V_{L_2}}$$

Snell's law provides the well-known relationship between angles of incidence and refraction for a wave impinging on an interface between two media with different indices of refraction. The law follows from the boundary condition that a wave be continuous across a boundary, which requires that the phase of the wave be constant on any given plane, resulting in $n_1 \sin \theta_1 = n_2 \sin \theta_2$ where $\theta_1$ and $\theta_2$ are the angles from the normal of the incident and refracted waves, respectively.

This same principle of scattering off a hollow shaft in two dimensions can be extrapolated to ultrasonic scattering off a mesh which produces three dimensional scattering. Generally, porosity produced in composite laminates is either discrete or takes on columnar shapes. Since graphite epoxy laminates consist of isotropic plies (0, 90, +45 and −45 degree plies) columnar voids can occur in any direction. Using a mesh, ultrasonic attenuation can be produced. The mesh, which mimics columnar porosity, is comprised of numerous arcs for the ultrasonic energy to scatter from which may result in scattering similar to that shown in the example of FIG. 7.

Figure 9:
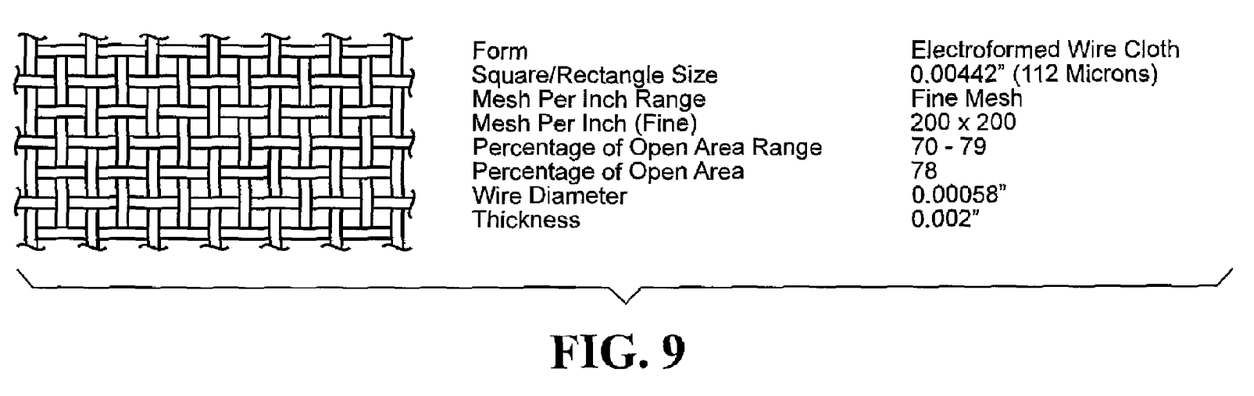
FIG. 9 is a woven mesh perform that may be incorporated into an embodiment of the present invention.
Figure 10:
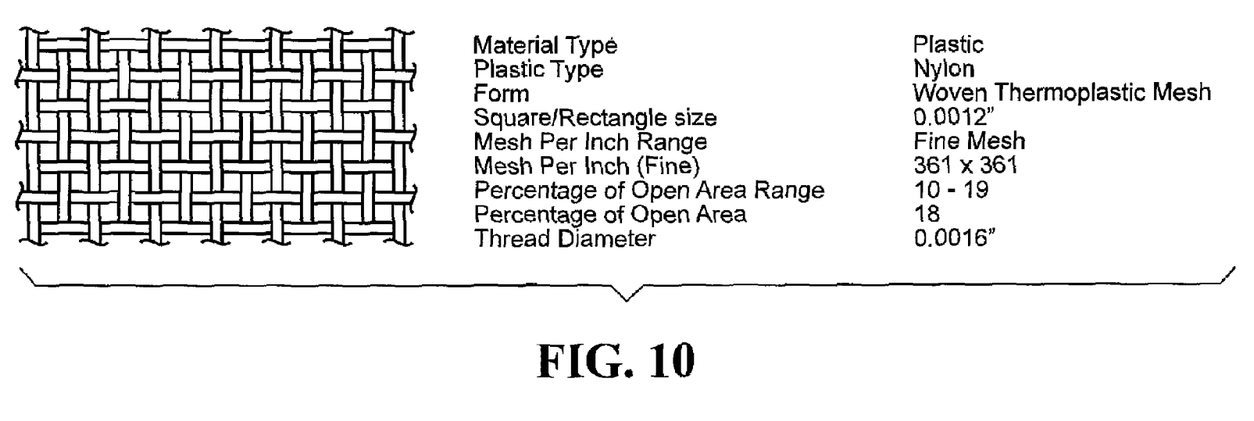
FIG. 10 is an example of another woven mesh perform that may be incorporated into another embodiment of the present invention.

The mesh may be of any size, shape, configuration, orientation, or material. Preferably, the mesh utilizes circumferential shapes to produce the desired scattering. FIGS. 9 and 10 depict examples of commercially available woven mesh performs that may be utilized. Each perform has unique acoustic properties based on a number of variables including the mesh's diameter, mesh range, percentage of open area and material type.

The core may comprise any size, shape, configuration, orientation, or material. For instance, the core may be made of at least one of a honeycomb, a balsa, a foam, a Foamcore, a web or truss core manufactured by WebCore under the product name TYCOR®, or other type of cored material known in the art. Preferably, the core is a solid layer, but in other embodiments, the core may comprise any number of differing numbers of core in differing configurations. In one embodiment, lengths of pencil lead may be used in a variety of diagonal arrangements to simulate the web and truss structures of TYCOR®. In another embodiment, the core may be made of the same material as the core of the cored composite laminate having porosity which is undergoing inspection. The core may aid in modeling the cored composite laminate having porosity.

Figure 11:
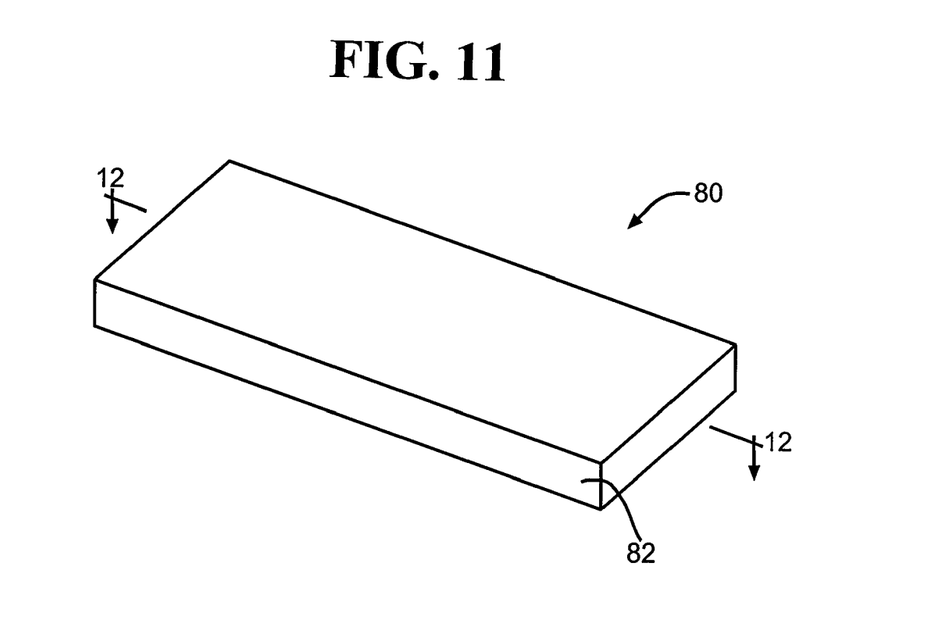
FIG. 11 is a side view of one embodiment of a reference standard under the present invention.
Figure 12:
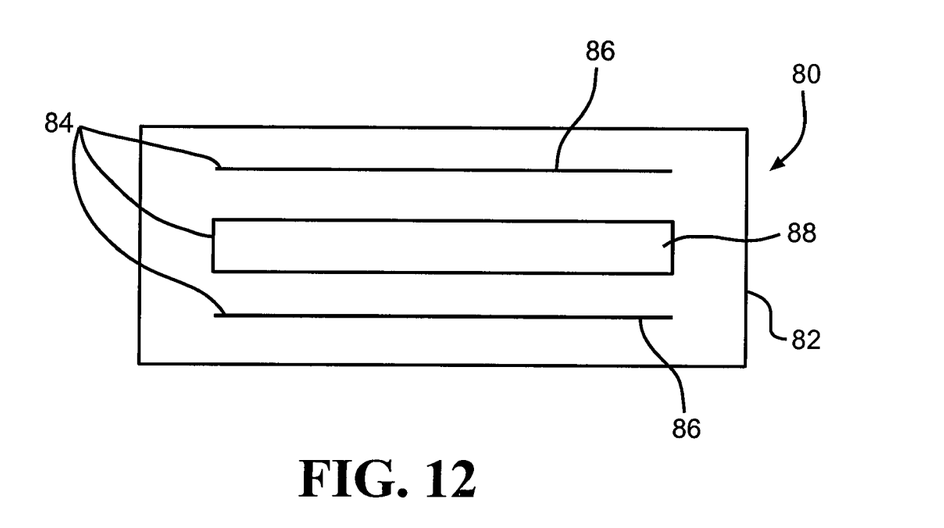
FIG. 12 is a partial cross-sectional view taken along line 12-12 of the embodiment of the present invention shown in FIG. 11.

To make the mesh useable as a scatting device, and the core useable to model a cored composite laminate, the mesh and core may be molded or inserted into a median that has similar acoustic properties of graphite epoxy. This may be accomplished by manufacturing a member out of a photopolymer resin using the SLA process. Narrow slots, comprising openings or holes, of uncured resin may be produced in the member during the SLA process. The width of the slots may approach the diameter or thickness of the mesh perform and core chosen for the application. In other embodiments, the slots may comprise varying sizes, orientations, and configurations. The mesh and core may be inserted into the uncured resin slots produced during the SLA process. Preferably, each mesh and core is inserted into its own uncured resin slot. In other embodiments, differing arrangements may be used. The member may then be subjected to a final ultraviolet cure to advance the cure of the pre-cured resin as well as to cure the uncured resin around the mesh and core to secure them in place. At least one of the mesh diameter, location, mesh range, percentage of open area, material, spacing, and type may be chosen to achieve equivalent ultrasonic attenuation of porosity for a graphite epoxy composite laminate, such as a cored composite laminate having porosity. Similarly, at least one of the type, size, configuration, location, spacing, and material of the core insert may be chosen to achieve equivalent ultrasonic attenuation or porosity for a cored composite laminate having porosity. FIGS. 11 and 12 illustrate side and cross-sectional views of a prototype standard 80 manufactured by utilizing the SLA process on a photopolymer resin to produce a member 82 having slots 84 within which alternating layers of meshes 86 and a core 88 are inserted. In other embodiments, the meshes 86 and core 88 may be disposed in, or about the member 82 in any configuration, orientation, numbers, or arrangement. For instance, more than one core 88 may be utilized in a variety of locations In one embodiment of the invention, an ultrasonic inspection process may start with designing and building a three-dimensional model of the standard, according to a porous, fiber-reinforced composite part to be inspected, such as a cored composite laminate having porosity. The porous cored composite laminate part to be inspected may comprise at least one of a honeycomb composite laminate having porosity, a balsa composite laminate having porosity, a foam composite laminate having porosity, a TYCOR® composite laminate having porosity, a Foamcore composite laminate having porosity, or other type of composite laminate having porosity. The three-dimensional model may be designed to include at least one slot to accommodate at least one mesh and at least one core at one or more locations where the resin will be uncured. Preferably, the model is designed to include multiple, layered slots each adapted to contain at least one of the core or mesh. In other embodiments, varying arrangements may be utilized. At least one of the number, configuration, spacing, type, and size of the at least one slot, and/or at least one of the type, size, location, diameter, mesh range, percentage of open area, and spacing of the at least one mesh, and/or at least one of the type, size, configuration, location, spacing, and material of the at least one core insert may be predetermined prior to manufacture of the standard in order to provide the standard with at least one of the acceptable and rejectable ultrasonic properties of the porous cored composite laminate part to be inspected. In such manner, the designed reference standard may comprise substantially the ultrasonic properties of a porous fiber-reinforced cored composite laminate reference standard. The at least one slot may be designed to be located in a variety of locations at, on, or within the model. At other non-slot locations, the model may be designed to have solid surfaces where the resin will be cured using the SLA process. The model, which may be arrived at using computer-aided-drafting, may be loaded into a stereo lithography machine to manufacture the reference standard by curing a photopolymer resin with a laser. In other embodiments, varying types of resins, such as a fiber-free polymer resin, and varying types of processes may be used to manufacture the standard.

In curing the photopolymer resin, the laser may raster back and forth curing resin only in the areas where the model indicates material to be. The areas to be slotted, as designated by the model, may not be cured by the laser during the SLA process. The SLA process may result in a member having at least one thickness. The member may comprise any shape, configuration, or thickness. The thickness of the member may be a substantially equivalent thickness based on the material properties of the composite material to be inspected. As the member is being built up during the SLA process, the at least one slot of uncured resin at the designated areas of the member may be formed in accordance with the positioning of the slots of the model. After the areas around the at least one slot are formed in the member, at least one mesh and at least one core may be inserted into the at least one slot to allow the uncured resin to flow around the mesh and core. Preferably, multiple slots are used, each containing either a mesh or a core. In other embodiments, other arrangements may be utilized. The at least one slot may be located in a variety of locations against, on, or within the member. The SLA process may be continued to encase the at least one mesh and the at least one core in place against, on, or within the member. When the SLA process is finished, the standard may be given a post UV cure to harden the resin and complete manufacture of the standard.

The process may produce an ultrasonic reference standard, made of a fiber-free polymer resin member containing at least one mesh and at least one core insert. The manufactured standard may substantially mimic the ultrasonic properties of a porous cored composite laminate, allowing the replacement of fiber-reinforced porous cored composite laminate reference standards. A varying amount of attenuation, or porosity, may be produced in the standard to accomplish the desired ultrasonic reference standard.

The manufactured standard may be used to inspect a fiber-reinforced cored composite laminate part having porosity with an ultrasonic technique. For instance, the manufactured standard may be ultrasonically scanned using ultrasonic inspection, such as pulse-echo and through-transmission. Next, a porous, fiber-reinforced cored composite laminate may be ultrasonically scanned using the same technique. The data obtained from scanning the porous, fiber-reinforced cored composite laminate may be compared with the data obtained from scanning the manufactured standard. Based on the data, a decision may be made as to whether to accept or reject the cored composite laminate.

By using the combination of a fiber-free polymer resin member, at least one mesh, and at least one core in manufacturing the ultrasonic inspection reference standard, the reference standard may be manufactured at lower manufacturing cost, and in less time, using a method that does not require any tooling, as compared to many existing fiber-reinforced cored composite laminate reference standards. The manufactured ultrasonic inspection reference standard may substantially comprise the ultrasonic properties of a porous cored composite laminate reference standard made of varying materials. In such manner, the manufactured ultrasonic inspection reference standard may replace other porous cored composite laminate reference standards, which may also be referred to as second reference standards.

Using stereo lithography to produce slots adapted to contain at least one pre-determined mesh and at least one pre-determined core in a solid median member is of value because manufacturing costs may be roughly ten percent of the traditional cost of manufacturing cored composite standards with similar porosity. The ability to produce slots adapted to receive pre-determined mesh and pre-determined cores in particular patterns to mimic naturally occurring conditions makes this approach desirable in the manufacturing of pseudo porosity standards. Additionally, the nature of the manufacturing process, including its tailorability and repeatability, may enable the production of multiple reference standards having substantially equivalent acoustic properties to allow inspection of porous cored composite parts around the world. The cost of manufacturing and certification of prior art reference standards may be limited by utilizing the present invention. The process may become the foundation for the development of pseudo porosity standards to characterize ultrasonic equipment, and may replace current cored composite reference standards. The invention may be used for ultrasonic inspection of porous cored composite laminate parts used in the aircraft airframe industry, both commercial and defense, and in other non-aircraft applications.

It should be understood, of course, that the foregoing relates to exemplary embodiments of the invention and that modifications may be made without departing from the spirit and scope of the invention as set forth in the following claims.

We claim:

1. An ultrasonic inspection reference standard for cored composite laminates having porosity comprising:
   a member having at least one thickness, wherein said member is manufactured from a fiber-free polymer resin;
   at least one mesh;
   and at least one core,
   wherein at least one of:
   (a) said polymer resin is a photo-polymer resin;
   (b) said member is manufactured using a stereo lithography process;
   (c) said at least one mesh is made of at least one of wire, fiberglass, polymer, nylon, and a metallic material; and
   (d) each of said at least one mesh and said at least one core are disposed at least one of against and within said member.

2. The ultrasonic inspection reference standard of claim 1, wherein said polymer resin is substantially similar to the resin of a composite material to be inspected.

3. The ultrasonic inspection reference standard of claim 1, wherein said member comprises more than one thickness.

4. The ultrasonic inspection reference standard of claim 1, wherein said member is created using a 3D computer-aided-design model.

5. The ultrasonic inspection reference standard of claim 1, wherein said at least one thickness of said member is an equivalent thickness based on material properties of a composite material to be inspected.

6. The ultrasonic inspection reference standard of claim 1, wherein said reference standard contains at least one of the acceptable and rejectable ultrasonic properties of a cored composite laminate having porosity.

7. The ultrasonic inspection reference standard of claim 1, wherein said member is manufactured using a method that does not require any tooling.

8. The ultrasonic inspection reference standard of claim 1, wherein said ultrasonic reference standard is for at least one of a honeycomb composite laminate having porosity, a balsa composite laminate having porosity, a foam composite laminate having porosity, a TYCOR® composite laminate having porosity, and a Foamcore composite laminate having porosity.

9. The ultrasonic inspection reference standard of claim 1, wherein said member is defined by at least one slot in which at least one of said at least one mesh and said at least one core is positioned.

10. The ultrasonic inspection reference standard of claim 9, wherein said member is defined by multiple, layered slots each containing at least one of said at least one mesh and said at least one core.

11. The ultrasonic inspection reference standard of claim 9, wherein said at least one slot is disposed within said member.

12. The ultrasonic inspection reference standard of claim 1, wherein one or more of the type, location, diameter, mesh range, percentage of open area, and spacing of said at least one mesh is predetermined prior to manufacture of said reference standard to provide said reference standard with at least one of the acceptable and rejectable ultrasonic properties of said cored composite laminates having porosity.

13. The ultrasonic inspection reference standard of claim 1, wherein one or more of the type, size, configuration, location, spacing, and material of said at least one core is predetermined prior to manufacture of said reference standard to provide said reference standard with at least one of the acceptable and rejectable ultrasonic properties of said cored composite laminates having porosity.

14. The ultrasonic inspection reference standard of claim 1, wherein said reference standard is used to inspect a cored composite laminate part of an aircraft structure.

15. The ultrasonic inspection reference standard of claim 1, wherein said at least one core is made of at least one of a honeycomb, a balsa, a foam, a TYGOR®, and a Foamcore.

16. The ultrasonic inspection reference standard of claim 1, wherein said at least one core is made of a same material as said cored composite laminate having porosity.

17. An ultrasonic inspection reference standard for cored composite laminates having porosity comprising:
 a member having at least one thickness;
 at least one core; and
 at least one mesh, wherein said reference standard contains at least one of the acceptable and rejectable ultrasonic properties of a cored composite laminate having porosity;
 wherein at least one of
  (a) said member is manufactured from a fiber-free polymer resin using stereo lithography;
  (b) said reference standard is adapted to substantially contain the ultrasonic properties of a second reference standard for at least one of a honeycomb composite laminate having porosity, a balsa composite laminate having porosity, a foam composite laminate having porosity, a TYCOR® composite laminate having porosity, and a Foamcore composite laminate having porosity, and said ultrasonic inspection reference standard replaces said second reference standard;
  (c) said reference standard is used to inspect a cored composite laminate pad of an aircraft structure;
  (d) said at least one core is made of at least one of a honeycomb, a balsa, a foam, a TYCOR®, and a Foamcore; and
  (e) said at least one core is made of a same material as said cored composite laminate having porosity.

18. The ultrasonic inspection reference standard of claim 17, wherein said at least one mesh is made of at least one of wire, fiberglass, polymer, nylon, and a metallic material.

19. The ultrasonic inspection reference standard of claim 17, wherein said member is defined by at least one slot in which at least one of said core and said at least one mesh is disposed.

20. The ultrasonic inspection reference standard of claim 19, wherein said member is defined by multiple, layered slots each containing at least one of said at least one mesh and said at least one core.

21. The ultrasonic inspection reference standard of claim 17, wherein one or more of the type, location, diameter, mesh range, percentage of open area, and spacing of said at least one mesh is predetermined prior to manufacture of said reference standard to provide said reference standard with at least one of the acceptable and rejectable ultrasonic properties of said cored composite laminates having porosity.

22. The ultrasonic inspection reference standard of claim 17, wherein one or more of the type, size, configuration, location, spacing, and material of said at least one core is predetermined prior to manufacture of said reference standard to provide said reference standard with at least one of the acceptable and rejectable ultrasonic properties of said cored composite laminates having porosity.

23. An ultrasonic inspection process for cored composite laminates having porosity comprising the steps of:
 manufacturing a reference standard comprising a member having at least one thickness, at least one core, and at least one mesh;
 inspecting a cored composite laminate having porosity with an ultrasonic technique using said reference standard; and
 at least one of the following:
  (a) ultrasonically scanning said reference standard using an ultrasonic inspection technique; ultrasonically scanning said cored composite laminate having porosity using said ultrasonic inspection technique; and comparing data obtained from scanning said cored composite laminate having porosity with data obtained from scanning said reference standard;
  (b) creating a 3D CAD model of an ultrasonic inspection standard; and manufacturing said member from a photo-polymer resin using stereo lithography;
  (c) using an ultrasonic technique selected from the group consisting of pulse-echo technique and through-transmission technique to scan said reference standard and to scan said cored composite laminate having porosity; and
  (d) manufacturing said member from a fiber-free photo-polymer resin using a stereo lithography process; and replacing a second reference standard for cored composite laminates having porosity with said manufactured reference standard.

24. The ultrasonic inspection process of claim 23, wherein the member is manufactured from a photo-polymer resin using a stereo lithography process.

25. The ultrasonic inspection process of claim 23, further comprising the step of manufacturing at least one slot in said member and disposing at least one of said at least one core and said at least one mesh in said at least one slot.

26. The ultrasonic inspection process of claim 25, further comprising the step of manufacturing a plurality of slots in said member and disposing within each of said slots at least one of said at least one core and said at least one mesh.

27. The ultrasonic inspection process of claim 23, wherein said at least one mesh is made of at least one of wire, fiberglass, polymer. nylon, and a metallic material.

28. The ultrasonic inspection process of claim 23, wherein said at least one core is made of at least one of a honeycomb, a balsa, a foam, a TYCOR®, and a Foamcore.

29. The ultrasonic inspection process of claim 23, wherein one or more of the type, location, diameter, mesh range, percentage of open area, and spacing of said at least one mesh is predetermined prior to manufacture of said reference standard to provide said reference standard with at least one of the acceptable and rejectable ultrasonic properties of said cored composite laminate having porosity.

30. The ultrasonic inspection process of claim 23, wherein one or more of the type, size, configuration, location, spacing, and material of said at least one core is predetermined prior to manufacture of said reference standard to provide said reference standard with at least one of the acceptable and rejectable ultrasonic properties of said cored composite laminate having porosity.

31. The ultrasonic inspection process of claim 23, further comprising the step of deciding whether to accept or reject said cored composite laminate having porosity based on said data.

32. The ultrasonic inspection process of claim 23 wherein said at least one core is made of a same material as said cored composite laminate having porosity.

* * * * *